United States Patent [19]

Braksmayer

[11] Patent Number: 4,485,262

[45] Date of Patent: Nov. 27, 1984

[54] S-BUTYL BIS(3-HYDROXYPROPYL) PHOSPHINE OXIDE

[75] Inventor: Diza P. Braksmayer, Cranbury, N.J.

[73] Assignee: FMC Corporation, Philadelphia, Pa.

[21] Appl. No.: 382,255

[22] Filed: May 26, 1982

[51] Int. Cl.$^3$ ............................................. C07F 9/53
[52] U.S. Cl. ..................................................... 568/15
[58] Field of Search ........................................... 568/15

[56] References Cited

U.S. PATENT DOCUMENTS

| | | | |
|---|---|---|---|
| 3,269,963 | 8/1966 | Ilgemann et al. | 528/283 |
| 3,489,811 | 1/1970 | Drucker et al. | 260/606.5 |
| 3,629,365 | 12/1971 | Gardner | 528/283 |
| 3,639,506 | 2/1972 | Haaf | 528/283 |
| 3,716,580 | 2/1973 | Maier | 260/488 J |
| 3,931,104 | 1/1976 | Luders et al. | 260/45.85 R |
| 3,948,980 | 4/1976 | Dettmeier et al. | 260/488 J |
| 4,127,566 | 11/1978 | King et al. | 528/283 |
| 4,154,775 | 5/1979 | Axelrod | 528/283 |
| 4,287,119 | 9/1981 | Braksmayer et al. | 260/45.95 L |
| 4,346,236 | 8/1982 | Lee | 568/15 |

OTHER PUBLICATIONS

Arbuzov et al., Synthesis of Bifunctional Organophosphorus Compounds Communication 2. Addition of Butylphosphine to Unsaturated Compounds, Academy of Sciences, USSR, translated from Izvestiya Akademii Nauk SSSR, Otdelenic Khimicheskikh Nauk, No. 3, pp. 502-506, Mar. 1963.
Chemical Abstracts 97 199091m, (1982).

*Primary Examiner*—Helen M. S. Sneed
*Attorney, Agent, or Firm*—Robert D. Jackson; Eugene G. Horsky

[57] ABSTRACT s-Butyl bis(3-hydroxypropyl) phosphine oxide, useful as a flame retardant in plastic compositions, is described.

1 Claim, No Drawings

S-BUTYL BIS(3-HYDROXYPROPYL) PHOSPHINE OXIDE

The present invention relates to 3-hydroxyalkyl phosphine oxides which are useful as flame retardant compounds and in particular to s-butyl bis(3-hydroxypropyl) phosphine oxide.

Polyphenylene oxide is a well-known polymer which is used extensively in the manufacture of various commercial plastic compositions. Generally speaking, polyphenylene oxide compositions containing from 40 to 85 percent by weight polyphenylene oxide and from 60 to 15 percent by weight of a polystyrene resin exhibit the best overall combination of properties and these compositions are preferred. Such compositions are referred to herein as "polyphenylene oxide compositions".

With the current and future federal requirements obligating automotive manufacturers to improve the efficiency of their product and reduce fuel consumption, there is a substantial growth in the use of engineering plastics as a replacement for metal to achieve weight reduction. The use of polyphenylene oxide compositions in the transportation, electrical/electronic and appliance categories accounts for a majority of its volume, and polyphenylene oxide compositions are the dominant engineering thermoplastic in appliance use. Such compositions are in general characterized as being relatively stable thermally upon long exposure to processing temperatures and shear. Upon exposure to flame, however, they burn quite readily as would be anticipated from their relatively high styrene content. There is a substantial and increasing demand for flame retardant polyphenylene oxide compositions.

To improve flame retardant characteristics, polyphenylene oxide compositions have been compounded with flame retardant additives, that is, aromatic halogen compounds plus aromatic phosphates as described in U.S. Pat. No. 3,639,506. A preferred composition in accordance with that teaching comprises from 20 to 80% by weight of poly(2,6-dimethyl-1,4-phenylene) ether, 20 to 80% by weight of a high impact polystyrene (styrene modified with rubber) and from 3 to 25 parts by weight per 100 parts by weight of the polyphenylene oxide composition of a flame retardant combination of 1 part triphenyl phosphate and 3 to 4 parts of a heavily chlorinated biphenyl. U.S. Pat. No. 4,154,775 states that cyclic phosphates are, by themselves, an effective, non-plasticizing flame retardant additive for polyphenylene oxide compositions. Such additives, however, frequently degrade or cause degradation under processing conditions (extrusion at about 250° C.) resulting in poor mechanical performance of the thermoplastic polyphenylene oxide compositions themselves.

The known flame retardants for polyphenylene oxide compositions suffer generally from one or more deficiencies including low compatibility, low thermal stability or poor fire retardant behavior in molded polyphenylene oxide compositions. Additionally, a serious problem posed by aromatic halogen flame retardants in polyphenylene oxide compositions is attributable to acid formation, either due to or arising from light exposure or thermal degradation with the released acid then attacking metal components in end-use applications. Some aromatic halogen compounds are contraindicated as fire retardant additives due to toxicity problems of the compound, that is, mutagenicity.

An improved class of fire retardant compounds for polyphenylene oxide compositions are certain 3-hydroxyalkyl phosphine oxides disclosed in applicant's U.S. Pat. No. 4,287,119. These compounds can be represented by the formula:

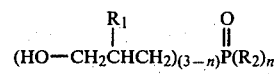

wherein $R_1$ may be the same or different radicals selected from the group consisting of hydrogen and the methyl radical, $R_2$ is an alkyl radical of 4 to 8 carbon atoms and n is either zero or one. The addition of a small but effective amount of these compounds to a thermoplastic polyphenylene oxide composition substantially improves the flame retardant properties of the polyphenylene oxide composition. The addition of the 3-hydroxyalkyl phosphine oxide to the polyphenylene oxide composition in the amount required to improve flame retardant properties does not adversely modify the physical properties of the polyphenylene oxide composition to a point where its commercial use is impaired. The 3-hydroxyalkyl phosphine oxides described above are readily compatible with polyphenylene oxide compositions and effective when added in small quantities, that is, 4 to 10 parts per hundred. Particularly preferred compositions are flame retardant polyphenylene oxide compositions to which have been added from about 4 to about 7 parts per hundred of a 3-hydroxyalkyl phosphine oxide.

The flame resistant polyphenylene oxide composition and 3-hydroxyalkyl phosphine oxide blends of the present invention are particularly advantageous for use in appliances, business machines, terminal strips, connectors and blocks.

The 3-hydroxyalkyl phosphine oxides of the present invention are more soluble in water than in polar organic solvents such as chloroform. Such 3-hydroxyalkyl phosphine oxides combine high compatibility in polyphenylene oxide compositions with high thermal stability and excellent fire retardant efficiency either alone or in combination with organo-halogen products.

The merits that may be attributed to the 3-hydroxyalkyl phosphine oxide flame retardant (relative to conventional flame retardant agents in present use) include no corrosion, high ultraviolet stability, non-toxicity and minimal adverse change in the physical properties of the polymer. The heat distortion temperature of the polyphenylene oxide composition is not appreciably altered by the addition thereto of 5 to 7 parts per hundred of a phosphine oxide flame retardant.

A particularly effective member of the alkyl bis(3-hydroxyalkyl) phosphine oxides aforesaid is s-butyl bis(3-hydroxypropyl) phosphine oxide which is compatible with polyphenylene oxide and polystyrene polymers and has improved mixing parameters that reduce polymer degradation by lowering the processing temperature. So far as is known, s-butyl bis(3-hydroxypropyl) phosphine oxide is a novel chemical compound and the provision of said compound constitutes the object and purpose of the invention.

The s-butyl bis(3-hydroxypropyl) phosphine oxide of the invention is prepared generally in the known manner of synthesizing 3-hydroxyalkyl phosphine oxides by first reacting a 3-hydroxy-1,2-unsaturated olefin such as allyl alcohol with phosphine in the presence of a free radical catalyst as described in U.S. Pat. No. 3,489,811.

The 3-hydroxyalkyl phosphine obtained by this process is readily converted to the corresponding phosphine oxide by oxidation with hydrogen peroxide.

The following examples will more fully illustrate the invention.

EXAMPLE I s-Butyl bis(3-Hydroxypropyl) Phosphine Oxide

Into a one gallon stainless steel pressure reactor is placed 0.5 g azobisisobutyronitrile dissolved in 600 ml of toluene. The reactor is purged with nitrogen and charged with 112 g (2.0 moles) of 2-butene and 102 g (3.0 moles, 50% excess) phosphine. The reaction mixture is heated and stirred at 85°–90° C. for one hour and maintained at that temperature with stirring while five 20 ml portions of azobisisobutyronitrile solution (5.5 g in 350 ml of toluene) are added at 20 minute intervals over 1 hour 40 minutes. No exotherm is noted during the catalyst addition and the pressure reading dropped from 190 psig (at the time of the first 20 ml catalyst addition) to 185 psig (20 minutes after the last catalyst addition).

The excess phosphine is vented from the reaction vessel and 278 g (4.8 moles, 20% excess) of allyl alcohol and 40 ml of the azobisisobutyronitrile catalyst solution is added to the reaction vessel. No exotherm is observed and heating is continued at 85°–90° C. with stirring and addition of 20 ml of azobisisobutyronitrile every 20 minutes until all of the catalyst solution (350 ml) has been added. The temperature is maintained with stirring at 85°–90° C. for 11 hours. A clear yellow liquid is removed from the reactor and heated to 100° C./1.0 mm to distill off the volatile materials. The residue is a clear yellow liquid weighing 290.9 grams. This residue is dissolved in an equal volume of isopropanol and oxidized with 30% hydrogen peroxide dissolved in an equal volume of isopropanol to give 308.2 g of a viscous yellow liquid (after removal of water and isopropanol) containing a small amount of a white suspended solid. The mixture is diluted with chloroform, filtered to remove the white solid, and the chloroform evaporated to leave a clear yellow liquid. The analysis of this liquid product is:

| Found (%) | Calculated for s-butyl bis(3-hydroxypropyl) phosphine oxide (%) |
|---|---|
| C = 54.50, 54.40 | 54.05 |
| H = 10.21, 10.21 | 10.36 |
| P = 13.28, 13.65 | 13.96 |

This product, which is believed to contain both s-butyl bis(3-hydroxypropyl) phosphine oxide and 3-hydroxypropyl di-s-butyl phosphine oxide, is evaluated as a fire retardant in polyphenylene oxide compositions (UL 94 Vertical Burn Test). The results are reported in Table I.

EXAMPLE II

Effect of s-Butyl bis(3-Hydroxypropyl) Phosphine Oxide As A Flame Retardant For Polyphenylene Oxide Compositions s-Butyl bis(3-hydroxypropyl) phosphine oxide is added to a polyphenylene oxide composition in the amounts per hundred parts of resin (PHR) indicated in Table I and dispersed throughout the resin. Mixing of the additive and resin is accomplished in a Haake mixer (HAAKE RHEOMIX MODEL 600 with REOCORD EU10 attachment, manufactured by Haake Inc., 244 Saddle River Road, Saddle Brook, N.J. 07662). The mixing takes place at 265° C. at which temperature some of the additive is volatilized. The Underwriter Laboratories rating (Vertical Burn Test) for the various combinations tested is indicated in Table I.

In testing the polyphenylene oxide compositions containing the flame retardant additive herein, the flame retardant properties are determined following procedures established by the Underwriter Laboratories Bulletin No. 94, STANDARD FOR TESTS FOR FLAMMABILITY OF PLASTIC MATERIALS FOR PARTS IN DEVICES AND APPLIANCES; Second Edition, Second Impression (as revised to Feb. 1, 1974) dated July 30, 1976. Test were run on ⅛-inch specimens and the Vertical Burn Test for classifying Materials 94 V-0, 94 V-1 or 94 V-2 and described in Section 3 of this publication is used. In this test, the V-0 rating indicates the best flame resistance and the V-1 rating indicates less flame resistance.

TABLE I

Effect of s-butyl bis(3-hydroxypropyl) phosphine oxide as a flame retardant in polyphenylene oxide compositions. All quantities are expressed in parts per hundred (PHR).

| A | B | C | D | E |
|---|---|---|---|---|
| 100 | — | 6.5 | — | V-0 |
| — | 100 | 4.25 | — | V-0 |
| — | 100 | — | 8 | V-1 |
| 100 | — | — | — | CB* |
| — | 100 | — | — | CB* |

A = 35 PHR polyphenylene oxide and 65 PHR polystyrene
B = 40 PHR polyphenylene oxide and 60 PHR polystyrene
C = s-butyl bis(3-hydroxypropyl) phosphine oxide
D = Mixed isopropylphenyl/phenyl phosphate esters
E = UL 94 Vertical Burn Test
CB* = Complete burn

I claim:
1. s-Butyl bis(3-hydroxypropyl) phosphine oxide.

* * * * *